United States Patent
Boutry-Duthil (10) Patent No.: US 10,272,268 B2
(45) Date of Patent: Apr. 30, 2019

(54) METHOD FOR ESTIMATING THE DOSE ADMINISTERED BY AN EXTERNAL RADIOTHERAPY SYSTEM

(71) Applicant: SAS D.R.E.A.M., Toulouse (FR)

(72) Inventor: Christine Boutry-Duthil, Mervilla (FR)

(73) Assignee: SAS D.R.E.A.M., Toulouse (FR)

(*) Notice: Subject to any disclaimer, the term of this patent is extended or adjusted under 35 U.S.C. 154(b) by 227 days.

(21) Appl. No.: 15/311,014

(22) PCT Filed: May 22, 2015

(86) PCT No.: PCT/EP2015/061393
§ 371 (c)(1),
(2) Date: Nov. 16, 2016

(87) PCT Pub. No.: WO2015/177343
PCT Pub. Date: Nov. 26, 2015

(65) Prior Publication Data
US 2017/0106215 A1    Apr. 20, 2017

(30) Foreign Application Priority Data
May 22, 2014    (FR) .................................... 14 54631

(51) Int. Cl.
*G06T 5/00*    (2006.01)
*G06T 7/00*    (2017.01)
(Continued)

(52) U.S. Cl.
CPC ......... *A61N 5/1071* (2013.01); *A61N 5/1031* (2013.01); *A61N 5/1049* (2013.01);
(Continued)

(58) Field of Classification Search
CPC ..................................................... G06T 5/002
See application file for complete search history.

(56) References Cited

U.S. PATENT DOCUMENTS 6,345,114 B1 * 2/2002 Mackie ............... A61N 5/1048
378/65
6,636,622 B2 * 10/2003 Mackie ............... A61N 5/1048
378/145
(Continued)

FOREIGN PATENT DOCUMENTS

EP         2248551 A1 * 11/2010 ........... A61N 5/1048
WO  WO-2015177343 A1 * 11/2015 ........... A61N 5/1031

OTHER PUBLICATIONS

Van Esch et al., "The use of an aSi-based EPID for routine absolute dosimetric pre-treatment verification of dynamic IMRT fields", Radiotherapy and Oncology, 71, (2004), pp. 223-234.
(Continued)

*Primary Examiner* — Gandhi Thirugnanam
(74) *Attorney, Agent, or Firm* — Pearne & Gordon LLP (57) ABSTRACT

The invention relates to a method for estimating the dose administered by an external radiotherapy system. The portal image supplied by the EPID detector is converted into a dose at a depth of reference in water, by means of a simple conversion formula.
Conversely, the corresponding portal image can be determined from a distribution of a nominal dose, under the same irradiation conditions. The invention can especially be applied to the verification of a treatment plan.

13 Claims, 8 Drawing Sheets

(51) Int. Cl.
*A61N 5/10* (2006.01)
*H04N 5/357* (2011.01)

(52) U.S. Cl.
CPC ............ *A61N 5/1075* (2013.01); *G06T 5/002* (2013.01); *G06T 7/0012* (2013.01); *H04N 5/357* (2013.01); *A61N 2005/1054* (2013.01); *G06T 2207/20224* (2013.01)

(56) References Cited

U.S. PATENT DOCUMENTS

| | | | | |
|---|---|---|---|---|
| 7,024,026 | B1* | 4/2006 | Ritt | A61N 5/1048 382/128 |
| 8,130,905 | B1* | 3/2012 | Nelms | A61N 5/1075 378/65 |
| 8,565,860 | B2* | 10/2013 | Kimchy | A61B 5/055 250/363.01 |
| 8,605,857 | B1* | 12/2013 | Renner | A61N 5/1071 378/65 |
| 8,948,842 | B2* | 2/2015 | Raleigh | A61B 5/0037 382/131 |
| 2002/0021830 | A1* | 2/2002 | Ritt | A61N 5/1048 382/132 |
| 2006/0159324 | A1* | 7/2006 | Ritt | A61N 5/1048 382/128 |
| 2008/0281181 | A1* | 11/2008 | Manzione | A61B 6/032 600/407 |
| 2009/0129659 | A1* | 5/2009 | Deutschmann | A61N 5/1048 382/132 |
| 2011/0052036 | A1* | 3/2011 | Valdivieso Cacique | A61N 5/1031 382/132 |
| 2011/0135190 | A1* | 6/2011 | Maad | A61B 6/0407 382/154 |
| 2013/0188856 | A1* | 7/2013 | Adler, Jr. | A61B 6/12 382/132 |
| 2014/0105355 | A1* | 4/2014 | Toimela | A61N 5/103 378/41 |
| 2015/0003711 | A1* | 1/2015 | Winfield | A61N 5/1071 382/132 |
| 2015/0343241 | A1* | 12/2015 | Han | A61N 5/1075 378/205 |
| 2016/0361570 | A1* | 12/2016 | Sayeed | A61N 5/031 |

OTHER PUBLICATIONS

Peter Winkler, "Dose-response characteristics of an amorphous silicon EPID", Med. Phys. 32, (10), Oct. 2005, pp. 3095-3105.
Peter Winkler, et al., "Implementation and validation of portal dosimetry with an amorphous silicon EPID in th energy range from 6 to 25 MV", Phys. Med. Biol. 52, (2007), pp. N355-N365.
Benjamin E. Nelms et al., "Evaluation of a fast method of EPID-based dosimetry for intensity-modulated radiation therapy", Journal of Applied Clinical Medical Physics, vol. 11, No. 2 (2010), pp. 1-15.
Wouter van Elmpt et al., "A literature review of electronic portal imaging for radiotherapy dosimetry", Radiotherapy and Oncology 88, (2008), pp. 289-309.
Brian W. King et al., "A method for removing arm backscatter from EPID images", Med. Phys. 40, (7), Jul. 2013, pp. 071703-1-071703-9.
Daniel A. Low et al., "A technique for the quantitative evaluation of dose distributions", Med. Phys. 25, (5), May 1998, pp. 656-661.
L. N. McDermott et al., "Dose-response and ghosting effects of an amorphous silicon electronic portal imaging device", Med. Phys. 31, (2), Feb. 2004, pp. 285-295.
French International Search Report for PCT/EP2015/061393 dated Jan. 15, 2015.
International Search Report for PCT/EP2015/061393 dated Aug. 4, 2015.

* cited by examiner

METHOD FOR ESTIMATING THE DOSE ADMINISTERED BY AN EXTERNAL RADIOTHERAPY SYSTEM

TECHNICAL FIELD

This invention generally relates to the field of dosimetry in external radiotherapy. It can especially be applied to external radiotherapy systems provided with an electronic portal imaging device.

PRIOR ART

External radiotherapy systems are well known in prior art. They make it possible to administer a dose of high energy particles (of about a few MeV) to cancer tumours while sparing the healthy tissue in the vicinity. The ionising effects of these particles, whether by direct ionisation when these particles are charged or by indirect ionisation when they are not charged, cause the death of the irradiated cells, by lesion of the nucleic acids responsible for cell division and the synthesis of proteins.

External radiotherapy systems make use of an electron linear accelerator. In such a system, the electrons are released by an electron gun then accelerated by a high-frequency alternating field produced by a magnetron or a klystron. The interposition of a target made of tungsten leads to the production of a beam of photons that can reach about twenty MeV. Conventionally, through common use in language, the energy of the photons is generally measured in MV in radiotherapy.

Treating a tumour via external radiotherapy consists in administering a dose of given energy in a zone of a given spatial extent. In order to spare the healthy tissue in the vicinity, the dose is administered by irradiation under several predetermined angles of exposition, with a basic dose being administered for each angle. Furthermore, for each angle of exposure, the beam emitted by the source of photons is collimated according to a particular profile in such a way as to reduce as much as possible the irradiation of healthy tissue. It is therefore necessary to precisely plan the angles of exposure, the beam profiles and the doses to be administered for each one of these angles. In practice, the treatment is simulated using a treatment planning station (TPS) for each patient. This station makes it possible to determine from three-dimensional anatomical images of the patient acquired using a radiological scanner (CT), the angles of exposure as well as the beam profile and the dose for each angle.

This radiotherapy technique, adapted to the three-dimensional geometry of the tumour is also called "conformal radiotherapy". Other technical advances have recently come to light, in particular that provided by intensity modulated radiotherapy (spatial and temporal) of the beam (IMRT) or arc therapy VMAT (Volumetric Modulated Arc Therapy).

Regardless of the radiotherapy technique under consideration, it is particularly important to verify that the doses effectively administered to the patient are indeed compliant with those provided for during the treatment planning, in order to ensure not only that the total dose administered to the tumour is indeed that which is sought but also that the dose gradient setpoint between cancer tissue and healthy tissue has indeed been respected. A method for verifying the dose administered to a patient in a conformal radiotherapy system is described in patent application EP-A-2 248 551.

Many pieces of hardware and software are currently available on the market to carry out dosimetric controls.

Recent external radiotherapy systems are generally provided with an electronic portal imaging device (EPID). An imaging device is defined as a device adapted to acquire images from a treatment field in radiotherapy. The images obtained as such, called portal images, show the irradiated zone and make it possible to verify the positioning of the patient in the treatment field.

Figure 1:
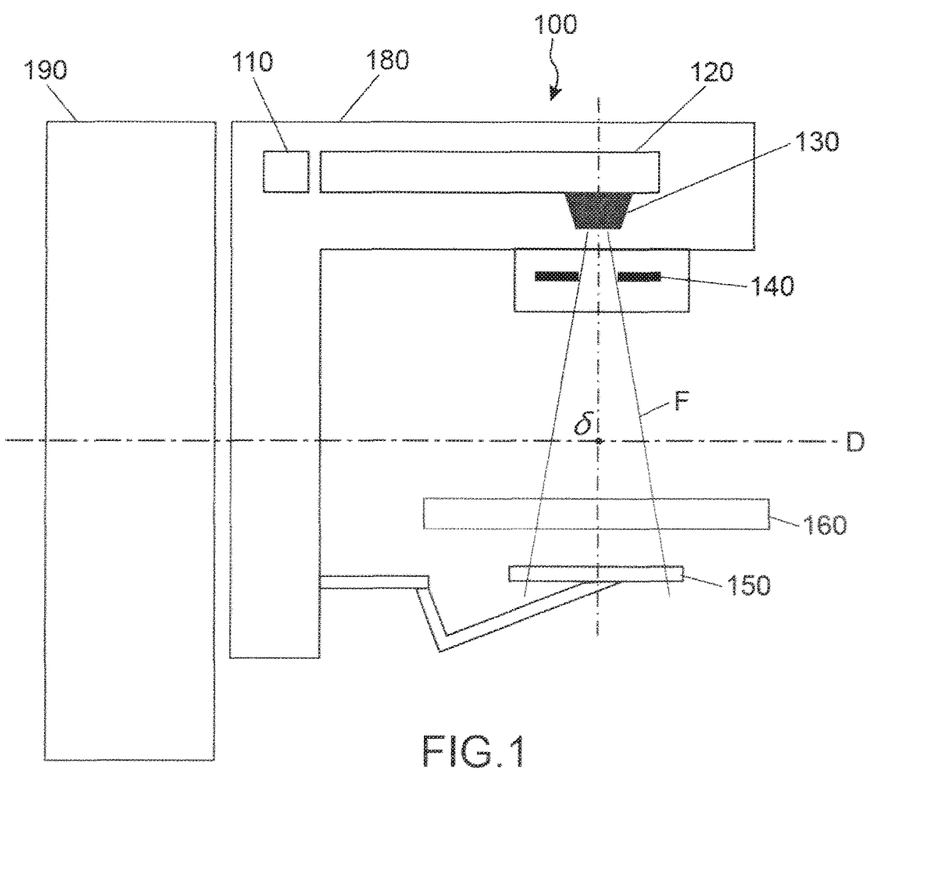
FIG. 1 diagrammatically shows an external radiotherapy system provided with a portal imaging device, known in prior art.

FIG. 1 diagrammatically shows an external radiotherapy system provided with an imaging device.

The external radiotherapy system comprises a linear accelerator, 120, powered by an electron gun, 110 and ending by an accelerator head (not shown). The electron gun and the linear accelerator are integrated into a mechanical arm 180, capable of rotating about an axis D, integral with a gate 190. In the head of the accelerator are in particular mounted the target 130, a primary collimation system, an equalizing cone beam and a secondary multi-blade collimation system, 140. The target (made of tungsten), bombarded by the electrons coming from the accelerator, constitutes the source of X photons. The portal imaging device, 160, is also integrated into the mechanical arm, on the side opposite the source of photons. As such, during the rotation of the arm, the portal imaging device is always placed in a plane orthogonal to the main axis of the beam. During treatment, the patient is lying on a table, referred to as a treatment table, 160, located between the source and the portal imaging device. The point of intersection, δ, between the axis of rotation of the mechanical arm, D, and the main axis of the beam, F, is called the isocentre of the system.

The latest generation of portal imaging devices use an amorphous silicon detector. There are different types of amorphous silicon detectors, those with direct detection and those with indirect detection. Those with direct detection do not use a fluorescent screen but directly a photoconductor that converts the X rays into electrical charges. However, those with indirect detection use a fluorescent screen to convert the incident photons into visible photons, with these visible photons than being converted into electrical charges forming the signal to be measured.

Figure 2:
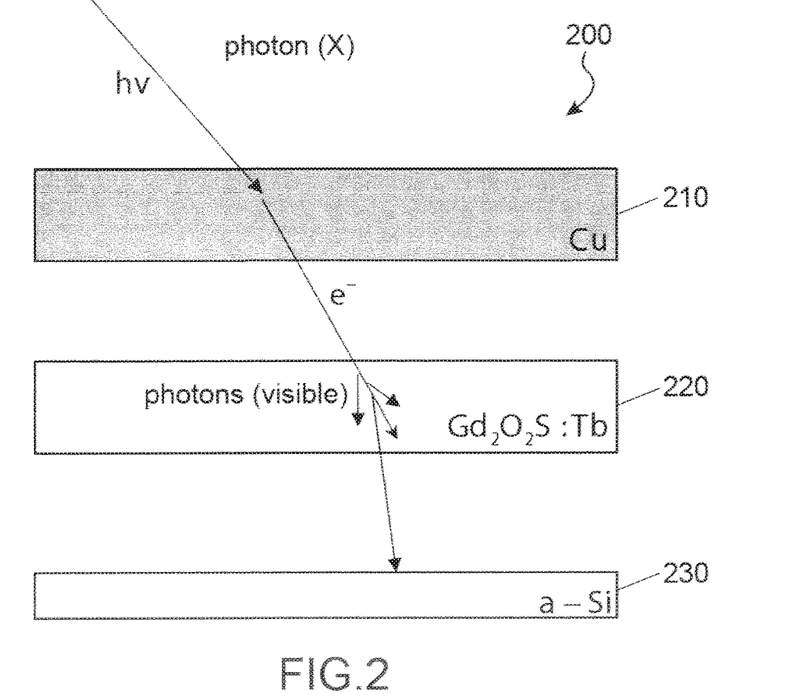
FIG. 2 diagrammatically shows a known example of a detector used in the external radiotherapy system of FIG. 1.

FIG. 2 diagrammatically shows an amorphous silicon detector with indirect conversion, known in prior art.

This detector comprises a metal plate, generally copper 210, wherein the incident X photons (primary photons) transfer a portion of the energy to electrons via the Compton effect. These electrons strike a phosphorus scintillator or a fluorescent screen, for example made of terbium-doped gadolinium oxide sulphide ($Gd_2O_2S$:Tb), 220, in order to generate therein photons in the visible range (secondary photons).

These secondary photons create electron-hole pairs in a layer of amorphous silicon, 230, to which is applied an electric field. The electric current generated by the electron-hole pairs is proportional to the incident light flow.

The detector is pixelated in that the layer of amorphous silicon comprises an array of photodiodes. The charges generated in the amorphous silicon are read by the array of field effect transistors using line electrodes and column electrodes. Each pixel as such supplies a value that can be digitised and represented by a grey level. An array of numerical values or frame is as such obtained.

The reading of the frames is carried out at given frequency (frame rate) and the doses are administered in the form of successive calibrated pulses with given repetition rate. The frames can be recorded one by one (referred to as continuous mode) or averaged over time (referred to an integrated mode). In this latter mode, it is understood that a portal image in fact represents an average over time of the charges generated in the amorphous silicon during a period of exposure of the beam. The portal image is displayed on the imaging device of the EPID in grey levels.

All of the difficulty in dosimetry then consists in obtaining the dose administered (more precisely the dose of photons arriving on the detector) or dose image from the portal image.

In practice, the dose administered is connected to a quantity of monitor units or MU. A monitor unit is a machine unit that sets the duration of the irradiation, for a given duration and frequency of the pulses of irradiation. The radiotherapy system is calibrated in such a way that one monitor unit corresponds to a predetermined deposited dose (generally 1 cGy) in a water phantom, at a depth of reference, $z_{ref}$, on the axis of the beam, for a field size of 10×10 cm², with the upper surface of the water phantom being located at a reference distance (for example 100 cm) from the source of photons. The calibration protocol is described in the report TRS398 by AIEA, June 2000. Recall that a Gray is a unit of energy deposited in relation to the mass. The energy deposited at a depth z is the difference between the energy that enters into a small volume of height dz at the depth z and the energy that exits from this small volume. The dose at the depth z is given by $$D = \frac{dE}{\rho S dz}$$

where dE is the aforementioned difference in energy at the depth z and ρSdz is the mass to which it relates, S being the surface of the field and ρ the density of the irradiated material. The reference to a water phantom in radiotherapy is justified due to this high percentage of water in the human body.

Various methods have been proposed to convert the portal image into a dosimetry image.

A first method known under the model term "CU" is described in the article by Van Esch et al. entitled "The use of an a Si-based EPID for routine absolute dosimetry pre-treatment verification of dynamic IMRT fields" published in Radiotherapy and Oncology No. 71 (2004), pp. 222-234. This method supposes a linear relationship between the dose, the grey level in the portal image and the exposure time, i.e.:

$$\hat{D} = a \cdot N_g \cdot T_{irrad} \quad (1)$$

where $\hat{D}$ is the dose administered, estimated by the method, $N_g$ is the grey level of the pixel in the image and $T_{irrad}$ is the exposure time to the beam, a is a scaling factor.

A second method known under the model term "frames" is described in the article by McDermott et al. entitled "Dose response and ghosting effects of an amorphous silicon electronic portal imaging device" published in Med. Phys. Vol. 31, No. 2, February 2004. This method supposes a linear relationship between the dose administered, the grey level in the portal image and the total number of frames intervening in the portal image, i.e.:

$$\hat{D} = a \cdot N_g \cdot N_f + b \quad (2)$$

where $\hat{D}$ is the dose administered, estimated by the method, $N_g$ is the grey level of the pixel in the image, $N_f$ is the total number of frames intervening in the portal image, a is a scaling factor and b an offset value.

Other models have been proposed, in particular in the article by P. Winkler et al. entitled "Data response characteristics of an amorphous silicon EPID", published in Med. Phys., vol. 32, No 10, October 2005, pp. 3095-3105. This model is based on a non-linear relationship between the grey level in the portal image and the number of monitor units during a frame period, i.e.:

$$\frac{N_g}{UM} = a\ln(UM) + b \quad (3)$$

where, $N_g$ is the grey level of the pixel in the image, UM is the number of monitor units, and a,b are constants. In fact, as explained in the aforementioned article a correction of the dose administered must again be carried out in order to take the beam start-up into account.

Finally document U.S. Pat. No. 8,130,905 proposes a method for estimating the dose administered by an external radiotherapy system, from the portal image. This method comprises a step of image correction using a multiplication through a specific beam correction array, a step of convolution with redistribution core in order to obtain an equivalent dose in water from the dose in air, and finally a step of correcting the dose from a calibration chart.

However, none of these methods gives satisfactory results for low doses (doses administered at the detector less than a threshold of 40 cGy). However, the multiplication of angles of exposure in the current conformal radiotherapy techniques often result in administering doses that are less than the aforementioned threshold for a given exposure.

Furthermore, the values of doses administered, obtained from portal images, are no longer generally correct when moving away from the axis of the beam. Complex correction formulas are then used as described for example in the article by P. Winkler et al. entitled "Implementation and validation of portal dosimetry with an amorphous silicon EPID in the energy range from 6 to 25 MV", published in Phys. Med. Biol., vol. 52, 2007, pp. N355-N365.

The purpose of this invention is consequently to propose a method for verifying the dose administered by an external radiotherapy system provided with a portal imaging device, which does not have the aforementioned defects, in particular which makes it possible to obtain a correct estimate of the dose including when the latter is low.

DISCLOSURE OF THE INVENTION

This invention is defined by a method for estimating the dose administered by an external radiotherapy system provided with a portal imaging device, according to which:

(a) a portal image is acquired using the portal imaging device;

(b) the grey level, $N_g$, of the pixel is determined at the centre of the portal image, corresponding to the intersection of the portal imaging device with the axis of the irradiation beam;

(c) the dose administered by the system is calculated at a depth of reference $z_{ref}$) in water using $$\frac{D}{D_{10}^{eq}} = \alpha + \beta \ln\left(\frac{N_g}{N_{g,10}}\right)$$

where $N_{g,10}$ is the grey level of the pixel at the centre of the image, obtained for a dose and reference irradiation conditions, $D_{10}^{eq}$ is a predetermined constant dose and α, β are coefficients determined beforehand in a prior calibration phase.

Prior to the step (b) advantageously the background noise is removed from the portal image by subtracting from it an image acquired in the absence of irradiation, in order to obtain a noise-suppressed portal image.

Likewise, prior to the step (b), the noise-suppressed image can be corrected by removing from it a component due to the backscattering of the beam by the environment of the portal imaging device.

The prior phase of calibration advantageously comprises:
  a step of acquiring a plurality K portal images for a plurality of doses, $D^k$, k=1, ..., K, and in reference irradiation conditions;
  a step of removing the noise by subtracting from said portal images an image acquired in the absence of irradiation in order to obtain a plurality K of noise-suppressed images;
  a step of correcting noise-suppressed images in order to remove from them a component due to the backscattering by the environment of the imaging device;
  a step of calculating coefficients α, β from the values $$\frac{D^k}{D_{10}^{eq}}$$

and $$\ln\left(\frac{N_g^k}{N_{g,10}}\right),$$

k=1, ..., K.

The coefficients α, β are advantageously obtained from the values $$\frac{D^k}{D_{10}^{eq}}$$

and $$\ln\left(\frac{N_g}{N_{g,10}}\right),$$

k=1, ..., K using linear regression.

Said prior phase of calibration can further include a phase of validation of coefficients α,β comprising:
  a step of measuring the two-dimensional distribution of a dose administered at the depth of reference for each one of the doses at which the portal images were acquired, said step of measuring supplying a plurality K of measured dose images;
  a step of transforming acquired portal images into dose images, in order to supply a plurality K of calculated dose images;
  a step of comparing said measured dose images with said calculated dose images, with the coefficients α,β being validated in the event of a concordance between the first and the second.

According to an alternative each portal image k=1, ..., K is transformed into a dose image using the relationship $$\frac{\hat{D}^k(i,j)}{D_{10}^{eq}} = \alpha + \beta\ln\left(\frac{N_g^k(i,j)}{N_{g,10}}\right)$$

where $N_g^k(i,j)$ is the grey level of the pixel (i, j) of the kth portal image acquired.

The measured dose images and the calculated dose images can then be compared using an analysis of index γ.

The invention further relates to a method for verifying of treatment plan for an external radiotherapy system provided with a portal imaging device, with the treatment plan being defined by a plurality M of two-dimensional distributions of a dose at a depth of reference, with each two-dimensional distribution being associated with an angle of incidence, a quantity of monitor units and a conformation of the irradiation beam, with each two-dimensional distribution of a dose giving a nominal dose image, said method comprising the following steps:
  a portal image is acquired for each angle of incidence, quantity of monitor units and conformation of the irradiation beam, in such a way as to obtain the same plurality M of acquired portal images:
  the acquired portal images are transformed into dose images in order to supply a plurality M of calculated dose images;
  said calculated dose images are compared to the nominal dose images.

Prior to the step of transforming, the background noise is advantageously removed from the acquired portal images by subtracting from them an image acquired in the absence of irradiation.

Likewise, prior to the step of transformation, the acquired portal images noise-suppressed as such can be corrected, by removing from them a component due to the backscattering of the beam by the environment of the portal imaging device.

The comparison between the calculated dose images and the nominal dose images can be carried out using an analysis of index γ.

The prior phase of calibration can here also include:
  a step of acquiring a plurality K of portal images for a plurality of doses, $D^k$, k=1, ..., K, and in reference irradiation conditions;
  a step of removing noise by subtracting from said portal images an image acquired in the absence of irradiation in order to obtain a plurality K of noise-suppressed images;
  a step of correcting noise-suppressed images in order to remove from them a component due to the backscattering by the environment of the imaging device;
  a step (840) of calculating coefficients α, β from values $$\frac{D^k}{D_{10}^{eq}}$$

and $$\ln\left(\frac{N_g^k}{N_{g,10}}\right),$$

k=1, ..., K.

The coefficients α, β can advantageously be calculated from values $$\frac{D^k}{D_{10}^{eq}}$$

and $$\ln\left(\frac{N_g^k}{N_{g,10}}\right),$$

k=1, ..., K using linear regression.

BRIEF DESCRIPTION OF THE DRAWINGS

Other characteristics and advantages of the invention shall appear when reading a preferred embodiment of the invention in reference to the attached figures among which.

DETAILED DESCRIPTION OF PARTICULAR EMBODIMENTS

An external radiotherapy system shall be considered in what follows provided with a portal imaging device as described in the introductory portion. The portal imaging device can be with direct or indirect conversion. Regardless of the method of conversion, the primary or secondary photons generate electron-hole pairs in a pixelated semiconductor detector, for example an amorphous semi-conductor detector as known in prior art.

The method for estimating the dose administered by the system uses the image portal supplied by the imaging device. Dose means in what follows the energy deposited by the beam in the water by unit of mass, at a given depth of reference, $z_{ref}$. Conventionally this depth of reference is chosen equal to 5 or 10 cm, according to the quality of the beam, starting from the surface of the water.

The portal image is comprised of the average of $N_f$ successive frames over the duration of the exposure. Similarly, the dose administered at a point is the sum of the basic doses administered at this point during the duration of each one of the frames. It can be supposed that the dose per frame is constant and equal to an average dose $\tilde{D}$.

The method for estimating the dose administered is based, according to this invention, on an original model connecting the grey level of the portal image with the dose per frame. More precisely, it has been shown that the grey level of a pixel in a portal image was connected to the dose per frame, using the following relationship:

$$\frac{N_g}{N_{g,10}} = A\exp\left(B\frac{\tilde{D}}{\tilde{D}_{10}^{eq}}\right) \qquad (4)$$

where $N_g$ is the grey level in the portal image, $\tilde{D}$ is the dose administered by the radiotherapy system during the duration of a frame, A is a constant representing the response of the detector for a zero dose and B is a parameter that depends on the energy of the incident photons, representing the attenuation of the photons in the detector.

$N_{g,10}$ and $\tilde{D}_{10}^{eq}$ represent respectively the grey level at the centre of the portal image and the corresponding dose at this point, in reference conditions. In what follows, we shall reason by frames and the notations D and $D_{10}^{eq}$ shall be used for reasons of simplification Generally, the dose deposited at a given depth comprises a first component, referred to as primary component, resulting from the photons coming from the source and interacting for the first time with the material, and a component, referred to as the scatter component, resulting from photons that have already interacted a first time with the material. The scattered component depends in particular on the size of the irradiation field, in such a way that the dose deposited at a given depth does not vary only simply linearly with the fluence at the entry of the material.

On the other hand, it has been shown that there is a depth of water, referred to as equivalent depth and noted as $z_{eq}$, for which the response of the portal imaging device is proportional to the dose deposited at this depth and, this, regardless of the size of the irradiation field.

Figure 3A:
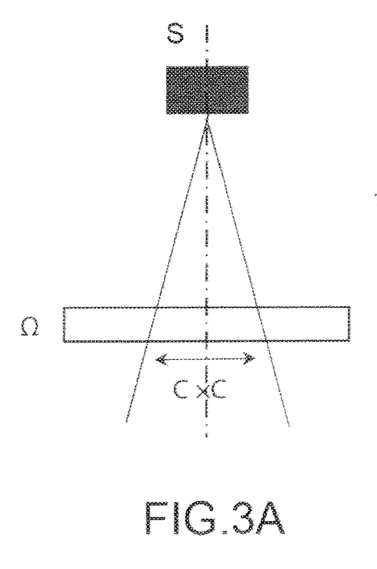
FIGS. 3A-3B show the way in which the equivalent depth is determined.
Figure 3B:
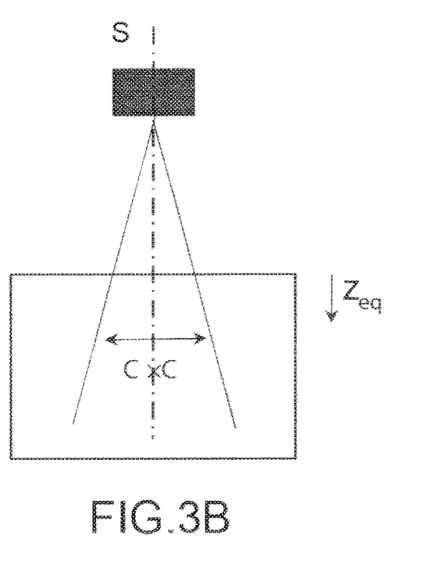

This situation of equivalence is shown in FIGS. 3A and 3B.

FIG. 3A diagrammatically shows the source of X photons emitting a beam F arriving on the detector Ω. It is supposed that the irradiation field of the beam is of a square size and of dimension C×C (expressed in cm²). The grey level at the centre of the portal image is noted as $N_g$.

FIG. 3B shows the same source S with this same beam of photons as in FIG. 3A. The beam is here incident on a water phantom. There is also the equivalent depth of water $z_{eq}$ in the terms defined hereinabove. The size of the irradiation field in the plane at the equivalent depth of water is C×C. This plane is chosen at a reference distance (here 100 cm) from the source.

The linearity of the response of the portal imaging device with respect to the dose administered results in:

$$\frac{N_g}{N_{g,10}} = \frac{D_c^{eq}}{D_{10}^{eq}} \qquad (5)$$

where $N_{g,10}$ is the grey level obtained for the conditions of calibration, namely for a field of size 10×10 cm² and a dose per frame corresponding to 100 MU.

The measurements show that the equivalent depth $z_{eq}$ varies with the energy of the incident photons but always remains less than the balanced depth $z_V$ in water. This results in that the equivalent depth cannot be used as a depth of reference.

The idea at the base of the invention is to deduce the response of the portal imaging device according to the dose administered at a depth of reference, $z_{ref}$, from the response of this imaging device according to the dose administered at the equivalent depth, $z_{eq}$.

This deduction can be obtained by proceeding with the steps of modelling shown in FIGS. 4A to 4D.

Figure 4A:
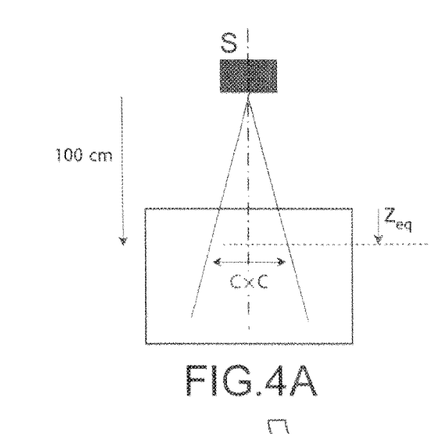
FIGS. 4A-4D show the steps of modelling that make it possible to estimate the dose administered by an external radiotherapy system from a portal image.

FIG. 4A simply uses FIG. 3B, in other words a water phantom of which the upper surface is located at 100 cm−$z_{eq}$ from the source of photons with a beam geometry such that the size of the irradiation field at the equivalent depth is C×C cm².

Figure 4B:
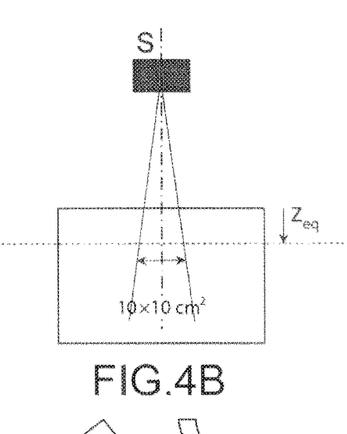

FIG. 4B shows the same situation as that of FIG. 4A with the difference that the size of the field is here the size of the reference field 10×10 cm². The beam consequently has a different divergence.

If $D_c^{eq}$ denotes the dose deposited in water at the equivalent depth $z_{eq}$ for a square beam of dimension C×C cm², and $D_{10}^{eq}$ the dose deposited in water at an equivalent depth but for an irradiation field of size 10×10 cm², there is the relationship:

$$D_c^{eq} = FOC_c^{eq}(C^2) \cdot D_{10}^{eq} \quad (6)$$

where $FOC_c^{eq}$ is the factor of opening of the collimator measured in water at the equivalent depth $z_{eq}$. Equivalently:

$$D_{10}^{eq} = D_c^{eq}/FOC_c^{eq}(C^2) \quad (7)$$

Figure 5A:
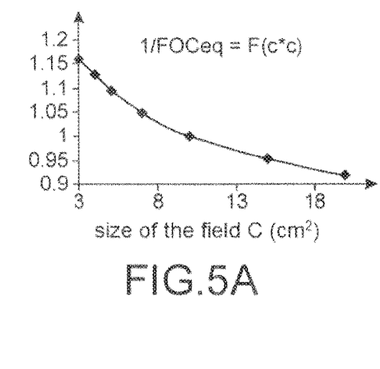
FIGS. 5A-5C respectively show the variation in the inverse of an opening factor of the collimator at the equivalent depth, of the tissue maximum ratio, and of the factor of the opening of the collimator at the depth of reference.

The variation of the inverse of the factor of opening of the collimator, $1/FOC_c^{eq}(C^2)$ according to the size of the field $C^2$ is given in FIG. 5A.

Figure 4C:
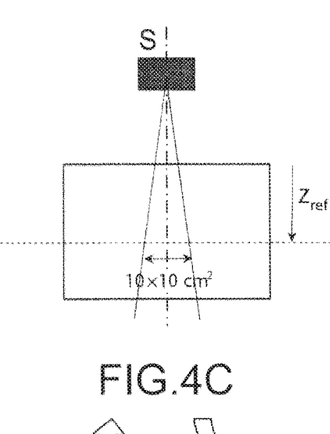

FIG. 4C shows the same situation as in FIG. 4B with the difference that the depth at which the dose deposited in the water is determined is no longer the equivalent depth $z_{eq}$ but the depth of reference $z_{ref}$. The relationship between the dose deposited in water at any depth and the maximum dose $D_{max}$ is referred to in dosimetry as the "tissue maximum ratio" (RTM).

Figure 5B:
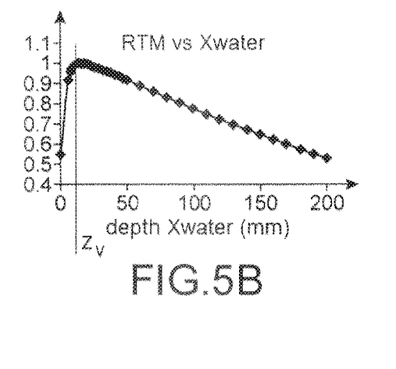

The ratio RTM varies according to the depth of the water according to the curve shown in FIG. 5B. This curve shows a first region, referred to as the build up region until a balanced depth $z_V$, at which the dose deposited reaches its maximum, then a second region, referred to as balanced region, wherein the dose deposited decreases exponentially.

In other words, the tissue maximum ratio is only the dose deposited, standardised by the maximum dose. There is consequently the relationship:

$$D_{10}^{eq} = RTM(z_{eq}) \cdot D_{max} \quad (8)$$

and, similarly:

$$D_{10}^{ref} = RTM(z_{ref}) \cdot D_{max} \quad (8')$$

where $D_{10}^{ref}$ is the dose deposited at the depth of reference in water, for reference irradiation conditions (distance from the source to the plane of 100 cm and size of the irradiation field of 10×10 cm² in this plane.

This results in:

$$D_{10}^{ref} = \frac{RTM(z_{ref})}{RTM(z_{eq})} \cdot D_{10}^{eq} \quad (9)$$

Figure 4D:
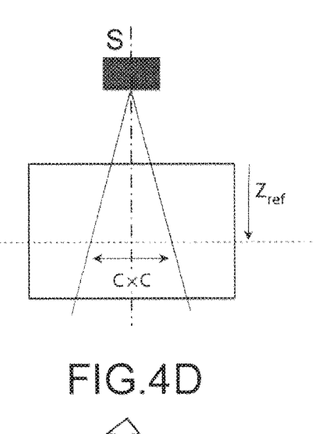

FIG. 4D shows the same situation as that in FIG. 4C with the difference that the beam now has a field size $C^2$ at the depth of reference, in other words the same field size as that of the beam in FIG. 4A.

Recall that the dose deposited at the depth of reference in the water phantom is the dose D that is sought to be estimated. The latter is connected to the dose $D_{10}^{ref}$ by the relationship:

$$D = FOC_c^{ref}(C^2) \cdot D_{10}^{ref} \quad (10)$$

where $FOC_c^{ref}$ is the factor of opening of the collimator, measured in water at the depth of reference $z_{ref}$.

It is deduced from equations (7), (9) and (10) that:

$$D = D_c^{eq} \cdot \frac{RTM(z_{ref})}{RTM(z_{eq})} \cdot \frac{FOC_c^{ref}(C^2)}{FOC_c^{eq}(C^2)} \quad (11)$$

Figure 5C:
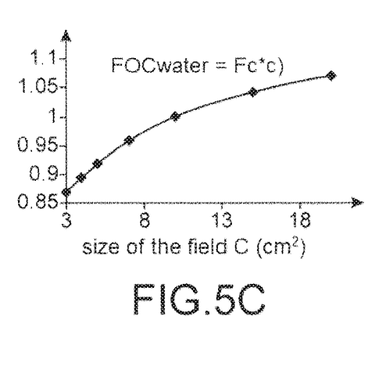

The variation of the opening factor of the collimator $FOC_c^{ref}$ according to the size of the field $C^2$ was shown in FIG. 5C.

It can be shown that the opening factor of the collimator at the depth of reference is linked to the opening factor of the collimator at the equivalent depth, according to a logarithmic law, in other words:

$$FOC_c^{ref} = \alpha' + \beta' \ln(FOC_c^{eq}) \quad (12)$$

where the constants $\alpha'$, $\beta'$ depend only on the energy of the incident photons.

This relation can be expressed, in light of (6), (9) and (10):

$$\frac{D}{D_{10}^{eq}} = \alpha + \beta \ln\left(\frac{D_c^{eq}}{D_{10}^{eq}}\right) \quad (13)$$

where $$\alpha = \alpha' \frac{RTM(z_{ref})}{RTM(z_{eq})} \text{ and } \beta = \beta' \frac{RTM(z_{ref})}{RTM(z_{eq})}.$$

Given that the grey level at the centre of the portal image is proportional to the dose measured at the equivalent depth, we have according to (5):

$$\frac{D_c^{eq}}{D_{10}^{eq}} = \frac{N_g}{N_{g,10}} \quad (14)$$

where $N_{g,10}$ is the grey level obtained for the conditions of calibration, namely for a field of size 10×10 cm² and a dose per frame corresponding to 100 MU.

It results from equations (13) and (14) that:

$$\frac{D}{D_{10}^{eq}} = \alpha + \beta \ln\left(\frac{N_g}{N_{g,10}}\right) \quad (15)$$

or, equivalently:

$$\frac{N_g}{N_{g,10}} = A\exp\left[B\frac{D}{D_{10}^{eq}}\right] \quad (16)$$

with $A=\exp(-\alpha/\beta)$ and $B=1/\beta$.

It is as such understood that it is possible, from the expression (15), to convert a portal image into an administered dose image. This conversion does not require convolution through a core or complex corrections according to the collimation of the beam.

Figure 6:
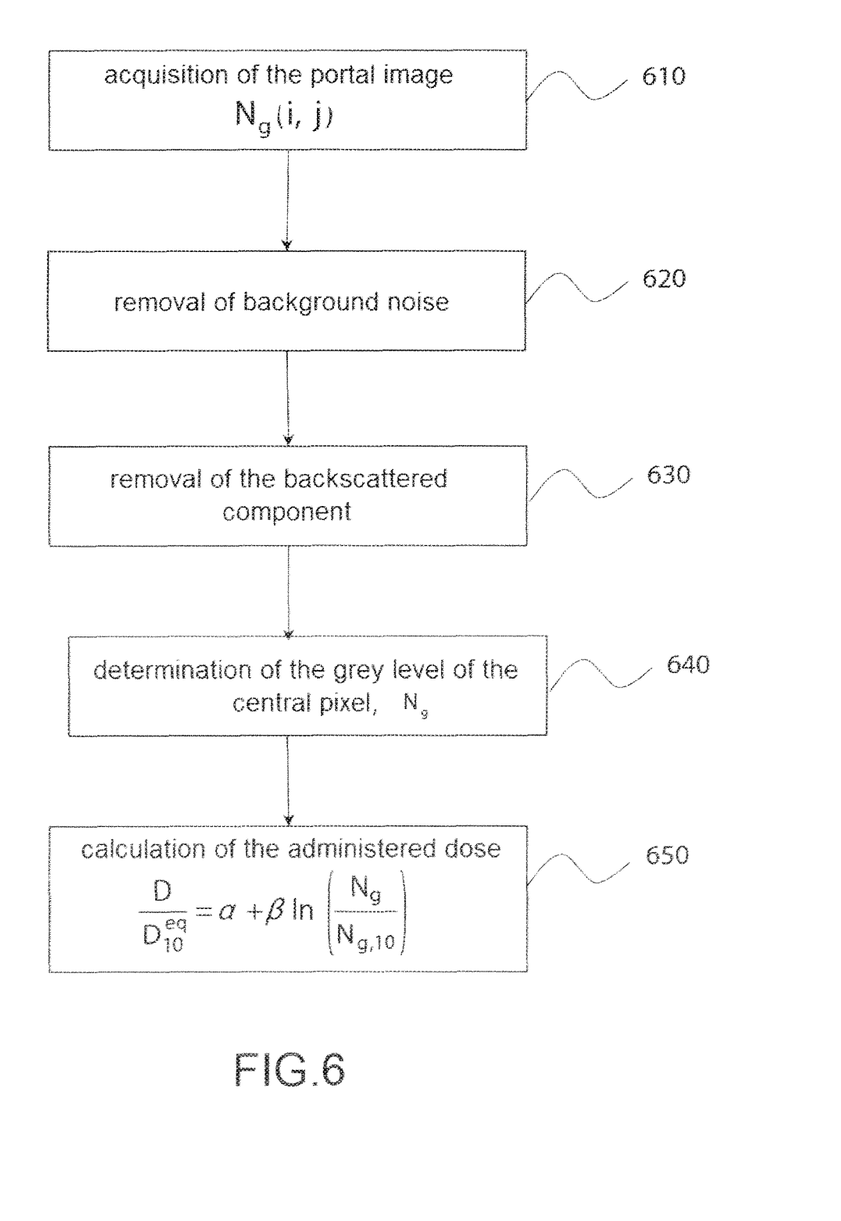
FIG. 6 diagrammatically shows the flowchart of a method for estimating the dose administered by an external radiotherapy system, according to an embodiment of the invention.

More precisely, FIG. 6 diagrammatically shows the method for estimating the dose administered by an external radiotherapy system, according to an embodiment of the invention.

In the step 610, a portal image is acquired in grey level using the portal imaging device. The image can be represented by an array $N_g$ of which the elements are grey levels $N_g(i,j)$ of the pixels of the image.

In the step 620, background noise is removed from the portal image, also referred to as dark field image (DFI). This image is obtained by having an acquisition carried out by the portal imaging device in the absence of irradiation. If $N_g^0$ is used to note the array of which the elements are the grey levels of the pixels in dark field, the operation of removing the background noise consists simply in calculating the array $N_g - N_g^0$, referred to as a noise-suppressed array.

In the step 630, the image noise-suppressed as such is corrected in order to take into account the radiation backscattered by the equipment of the radiotherapy system, in particular by the mechanical arm. The correction is carried out by removing from the image the component due to the backscattering. This correction can be carried out as described for example in the article by B. W. King et al. entitled "A method for removing arm backscatter from EPID images", published in Med. Phys., vol. 40, no. 7, July 2013, pp. 071703-1 to 071703-9.

In the step 640, the grey level, $N_g$, of the pixel is determined at the centre of the portal image, i.e. at the point of intersection of the portal image with the axis of the beam.

In the step 650, the dose administered, D, is calculated using the expression (15) from the grey level $N_g$, with the parameter $\alpha, \beta$ having been obtained using a prior calibration procedure described hereinbelow.

Note that if the steps 620 and 630 are required in order to obtain a precise estimate of the dose administered, they can be omitted when a rougher estimate is sufficient.

Figure 7:
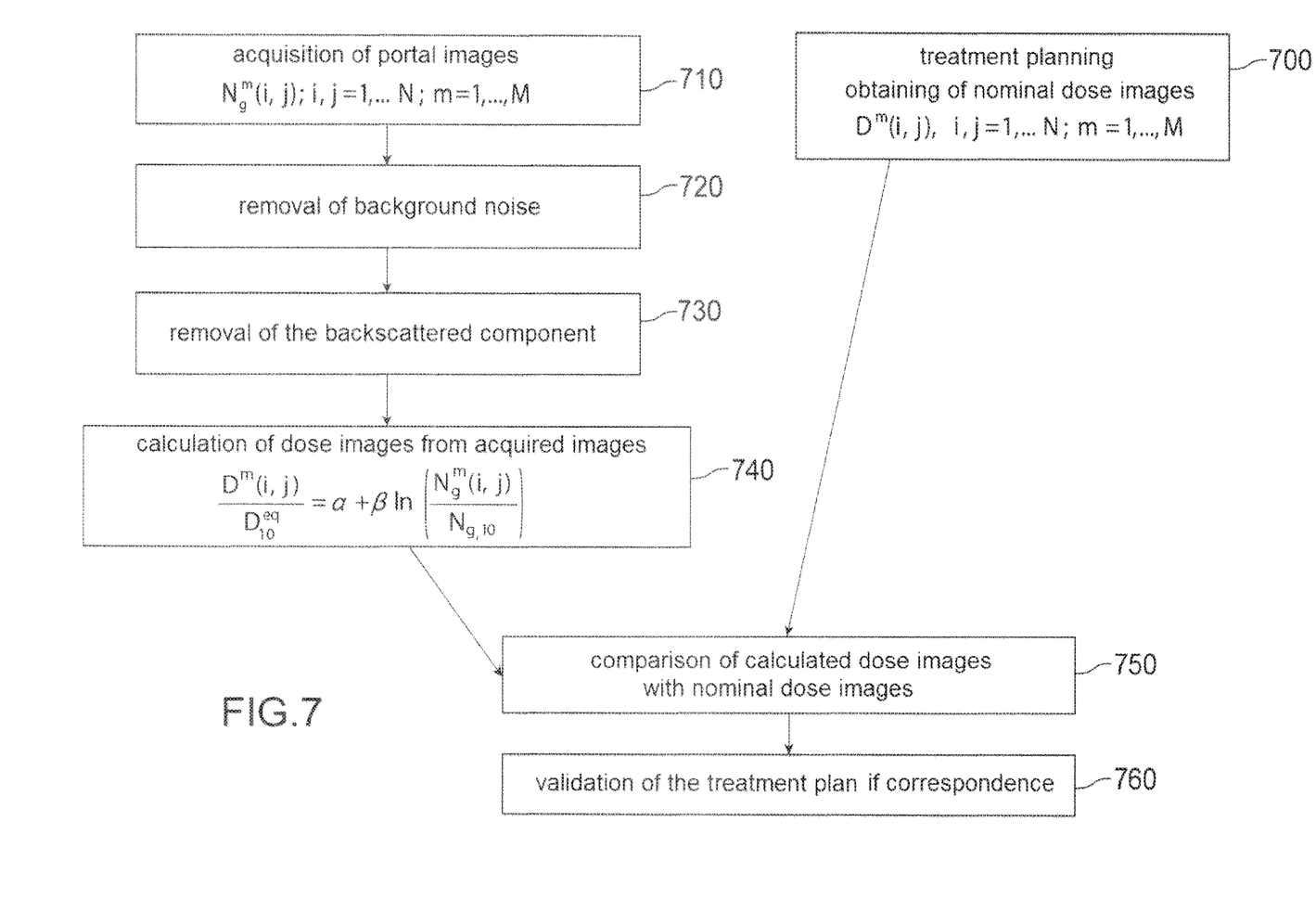
FIG. 7 diagrammatically shows the flowchart of a method for verifying a treatment plan by an external radiotherapy system.

FIG. 7 diagrammatically shows a method for verifying the dose administered by an external radiotherapy system, according to an embodiment of the invention.

This method can especially be applied in the framework of a radiotherapy treatment planning.

700 shows a step of treatment planning by external radiotherapy. This step consists in determining a plurality M of angles of incidence of the beam and for each angle of incidence a conformation of the beam (i.e. the arrangement of the blades of the collimator), a distance from the source to the treatment table and a quantity of monitor units. In other words, for each angle of incidence, a two-dimensional array of a dose is determined, $\overline{D}^m(i,j)$, $i,j=1,\ldots,N$, representing a mapping of the dose to be administered to the patient. This two-dimensional array of a dose can be represented as a nominal dose image $I^m$ of which each pixel of coordinates $(i,j)$ has for grey level the dose $\overline{D}^m(i,j)$.

In parallel, in 710, the acquisition is made, in the absence on the patient, of portal images of the beam using the EPID detector, under the different angles of incidence, according to the various conformations and with the number of MU specified in the treatment plan. Each portal image, $m=1,\ldots,M$ is defined by the grey levels of its pixels, i.e. $N_g^m(i,j)$ $j=1,\ldots,N$.

Each one of these images can be corrected, in 720, through the removal of the background noise, as described above, and, in 730, by the removal of the radiation backscattered by the equipment of the radiotherapy system.

In the step 740, the portal image is transformed into an administered dose image using the expression:

$$\frac{D^m(i,j)}{D_{10}^{eq}} = \alpha + \beta\ln\left(\frac{N_g^m(i,j)}{N_{g,10}}\right) \quad (17)$$

In step 750, each calculated dose image $D_m(i,j)$, $m=1,\ldots,M$, in the preceding step is compared with the nominal dose images $\overline{D}_m(i,j)$, $m=1,\ldots,M$, supplied by the treatment plan. The comparison of the calculated images with the nominal images is advantageously carried out using an analysis of index $\gamma$, known in the field of dosimetry and recalled further on.

In step 760, if the calculated dose images and the nominal dose images are concordant in terms of an analysis of index $\gamma$, the treatment plan is validated.

Those skilled in the art will understand that alternatively, the nominal dose images can be converted into nominal portal images using the relationship (16), and compare the acquired portal images with the nominal portal images. The comparison can also be done using an analysis of index $\gamma$.

Figure 8:
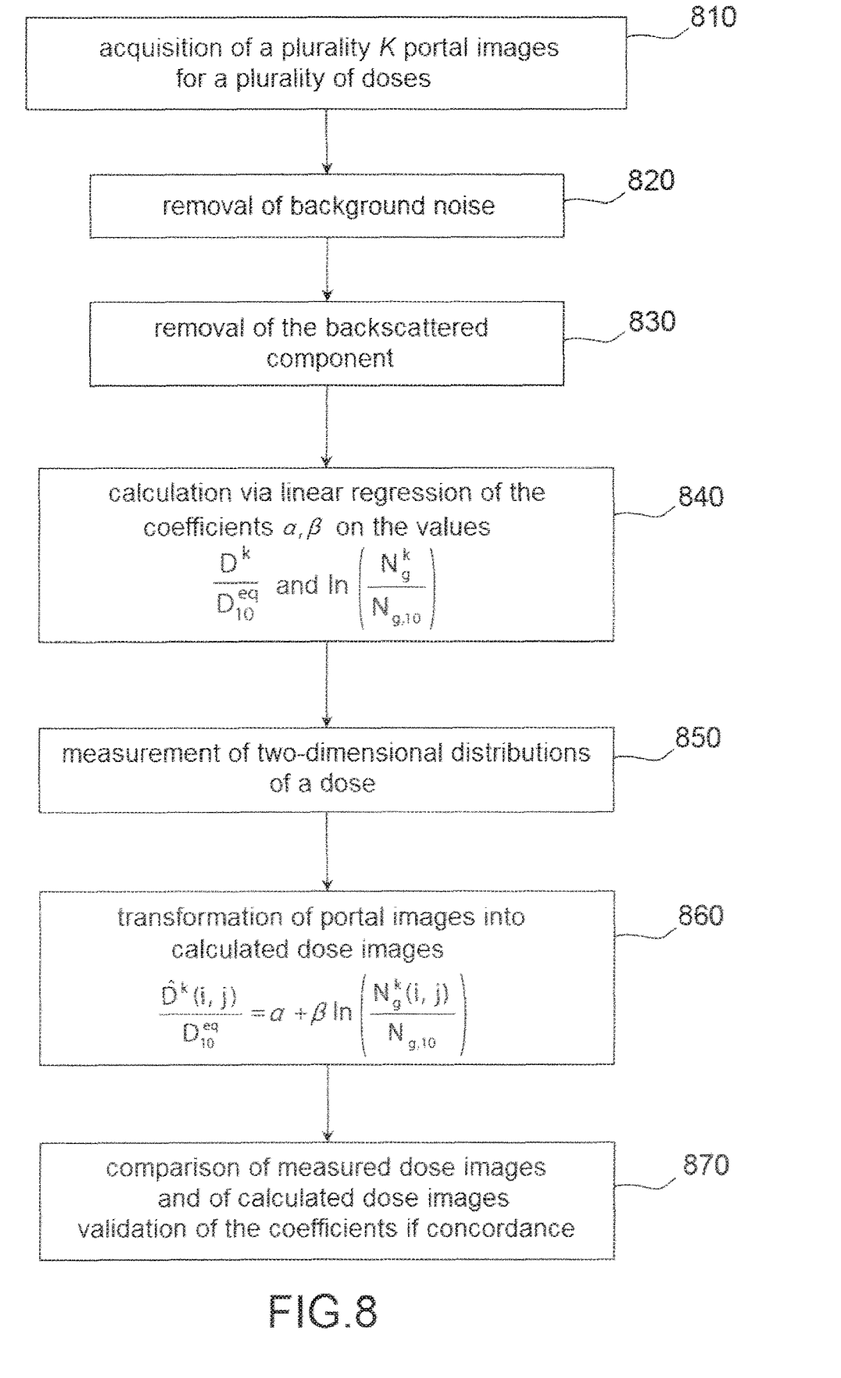
FIG. 8 diagrammatically shows the flowchart of a method of calibration for the method for estimating the dose administered according to FIG. 6 or the method for verifying a treatment plan according to FIG. 7.

FIG. 8 diagrammatically shows a method of calibration for the method for estimating the dose administered of FIG. 6 or the method of verifying the treatment plan of FIG. 7.

In the first step 810, a plurality K of images is acquired using the EPID detector of the external radiotherapy system. The images are acquired for a plurality of doses, for example doses varying from 2 to 400 MU. The acquisition is done in the absence of the patient, in reference irradiation conditions, i.e. with a beam conformed to have a square field of size 10×10 cm² on the detector. The detector is placed at a distance of 100 cm from the source of photons X.

In step 820, a first correction of the images acquired is carried out by removing the background noise as explained hereinabove, in relation with the step 620 of FIG. 6.

In step 830, a second correction of the images is carried out by removing images noise-suppressed as such the contribution of the radiation backscattered by the environment (in particular by the mechanical arm of the system). This correction is carried out as explained hereinabove in relation with the step 630 of FIG. 6.

In step 840, the coefficients $\alpha, \beta$ are calculated by carrying out a linear regression on the points of coordinates $$\frac{D^k}{D_{10}^{eq}}$$

and $$\ln\left(\frac{N_g^k}{N_{g,10}}\right),$$

$k=1,\ldots,K$ where $D^k$ is the dose per frame that was used to generate the image k, $N_g^k$ is the grey level of the pixel at the centre of the image k=1, ..., K (in other words on the axis of the beam), $N_{g,10}$ represents the grey level at the centre of the image for a dose per frame corresponding to a beam of 10×10 cm² and 100 MU.

Optionally, it can be verified that the coefficients α,β are indeed correct using the steps 850-870.

More precisely, in step 850, using an ionisation chamber, the two-dimensional distribution of the dose administered in water is measured (or simply the transversal profile of the dose in a plane of symmetry of the beam) at the depth of reference. This distribution can be measured for each one of the values of the dose at which the images were obtained in the step 810. As such, through the measurement, K two-dimensional distributions in dose are obtained. These K two-dimensional distributions can be considered as measured dose images, $D^k(i,j)$; i, j=1, ..., N; k=1, ..., K.

In step 860, the acquired portal images are transformed into calculated dose images using the relationship:

$$\frac{\hat{D}^k(i,j)}{D_{10}^{eq}} = \alpha + \beta \ln\left(\frac{N_g^k(i,j)}{N_{g,10}}\right) \quad (18)$$

where $N_g^k(i,j)$ is the grey level of the pixel (i, j) of the kth portal image acquired.

In step 870, the dose images calculated in the preceding step are compared with the dose images measured in the step 850. This comparison is carried out based on an analysis of index γ as indicated hereinabove.

When these images concord, the validity of the coefficients α,β can be concluded.

The method for comparing two images on the basis of the index γ is described in the article by D. A. Low et al. entitled "A technique for the quantitative evaluation of dose distributions" published in the review Med. Phys., Vol. 25, No. 5, pp. 656-661, and is recalled hereinafter.

The method for comparing based on an analysis of index γ makes it possible to compare an image with respect to a reference image. They can be represented respectively by two-dimensional variables I(x, y) (image to be compared) and $I_r(x, y)$ (reference image), these variables can for example be values of the dose or grey levels of portal images.

The two-dimensional variables I(x, y) and $I_r(x, y)$ can be represented by layers in a three-dimensional space, at each point of coordinates x, y being associated with an ordinate point I(x, y), resp. $I_r(x, y)$. In what follows the reference layer shall be called, $\Lambda_r$, the reference image layer and current layer, Λ, the layer of the image to be compared.

At each point P of $\Lambda_r$, of coordinates $(x_P, y_P, z_P = I_r(x_P, y_P))$ of the reference layer, an ellipsoid of revolution of radius $\delta r_{max}$ and of height $\delta I_{max}$ is positioned. It is then determined if there is a point Q of the current layer present in the ellipsoid.

More precisely, the index γ evaluated at the point of coordinates $(x_P, y_P)$ is given by:

$$\gamma(x_P, y_P) = \min_{Q \in \Lambda}\left[\sqrt{\left(\frac{\delta r}{\delta r_{max}}\right)^2 + \left(\frac{\delta I}{\delta I_{max}}\right)^2}\right] \quad (19)$$

where $\delta I = |I(x_Q, y_Q) - I_r(x_P, y_P)|$ and $\delta r = \sqrt{(x_Q - x_P)^2 + (y_Q - y_P)^2}$.

A value of index γ less than 1 indicates a concordance between the two images at the point under consideration.

Figure 9:
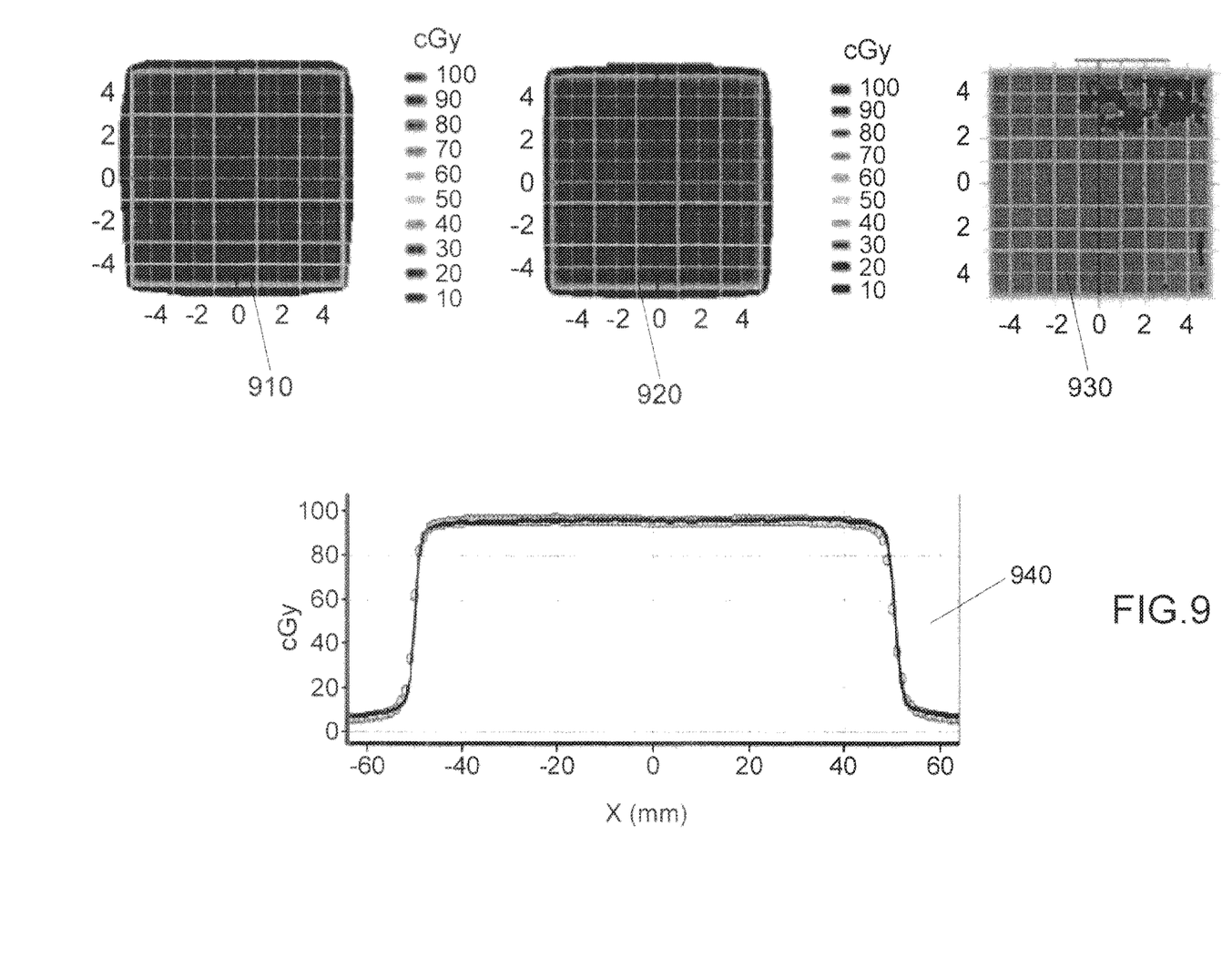
FIGS. 9 and 10 show comparisons by analysis of index γ between nominal dose images, coming from a treatment plan and calculated dose images from portal images.

FIG. 9 shows a comparison, by analysis in index γ, between a nominal dose image 910, coming from a treatment plan, and a dose image, calculated from a portal image, 920. The nominal dose is here uniform in the field of irradiation of size 10×10 cm², for 100 MU. The index γ is shown in 930. 940 shows the profiles according to the axis OX of the nominal dose image (solid line) and of the calculated dose image (circles). Note the good correspondence between the two profiles. Only a low portion of the image calculated has a slight distortion in relation to the nominal image, as shown in the image of index γ, 930 (portion at the upper right of the image). This slight distortion here comes from the absence of correction for the backscattered component.

Figure 10:
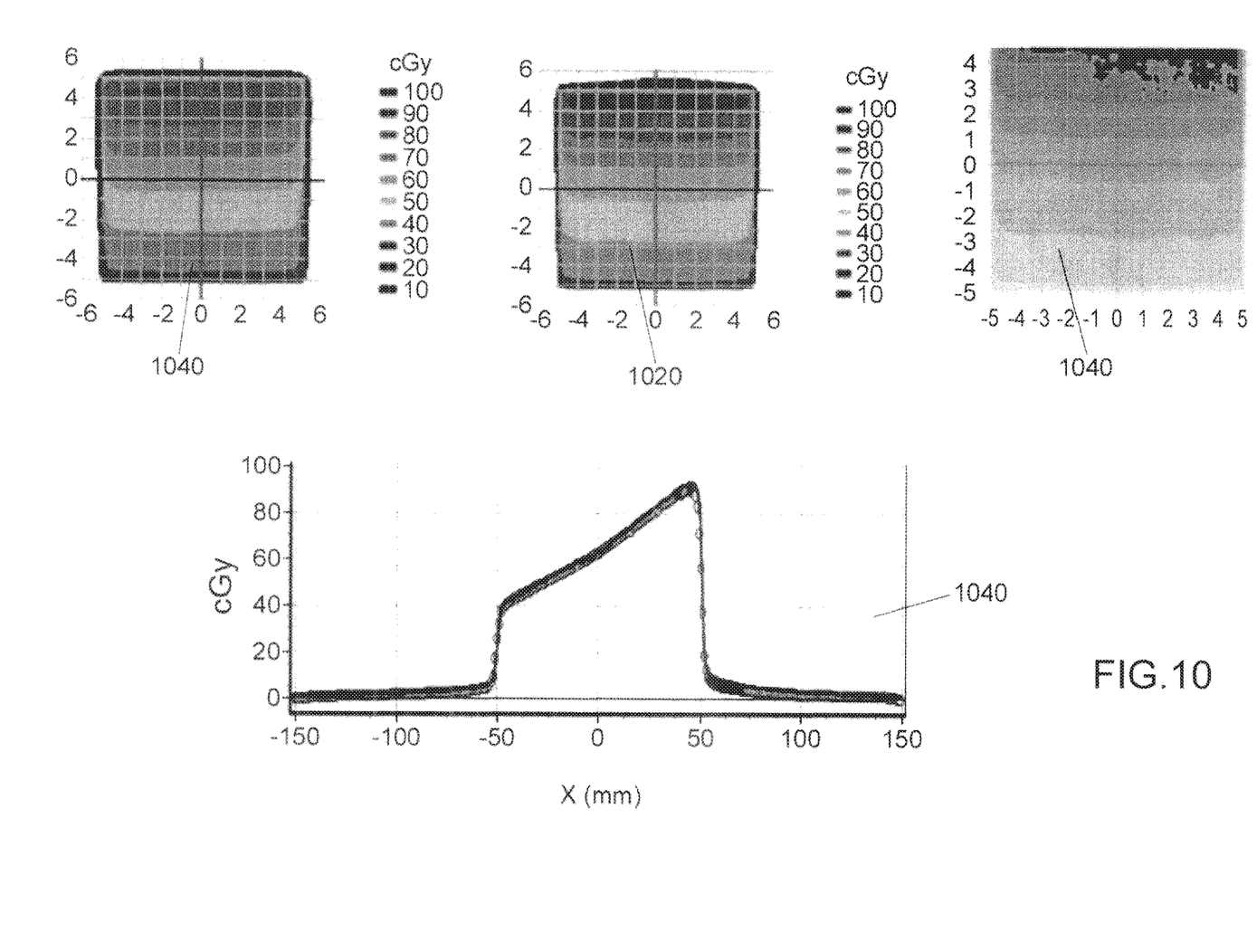

FIG. 10 shows a comparison, by analysis in index γ, between a nominal dose image 1010, coming from a treatment plan, and a dose image, calculated from a portal image, 1020. The nominal dose here has a gradient in the field of irradiation (100 MU, field of irradiation of size 10×10 cm² and filter in the corner directed at 60° in relation to the axis of the beam). The index γ is shown in 1030. 1040, shows the profiles according to the axis vertical of the nominal dose image (solid line) and of the calculated dose image (circles). Note the very good correspondence between the two profiles. Only a low portion of the calculated image has a slight distortion in relation to the nominal image, as shown in the image of index γ, 1030 (portion at the top of the image). As hereinabove, this slight distortion here comes from the absence of correction of the backscattered component.

The invention claimed is:

1. Method for estimating the dose administered by an external radiotherapy system provided with a portal imaging device, characterised in that:
   (a) a portal image is acquired (610) using the portal imaging device;
   (b) the grey level, $N_g$, of the pixel is determined (640) at the centre of the portal image, corresponding to the intersection of the portal imaging device with the axis of the irradiation beam;
   (c) the dose, D, administered by the system is calculated (650) at a depth of reference ($z_{ref}$) in water using $$\frac{D}{D_{10}^{eq}} = \alpha + \beta \ln\left(\frac{N_g}{N_{g,10}}\right)$$

where $N_{g,10}$ is the grey level of the pixel at the centre of the image, obtained for a dose and reference irradiation conditions, $D_{10}^{eq}$ is a predetermined constant dose and α, β are coefficients determined beforehand in a prior phase of calibration.

2. Method for estimating the dose according to claim 1, characterised in that, prior to the step (b) the background noise is removed (620) from the portal image by subtracting from it an image acquired in the absence of irradiation, in order to obtain a noise-suppressed portal image.

3. Method for estimating the dose according to claim 2, characterised in that, prior to the step (b), the noise-suppressed image is corrected (630) by removing from it a component due to the backscattering of the beam by the environment of the portal imaging device.

4. Method for estimating the dose according to claim 3, characterised in that said prior phase of calibration comprises:

a step (810) of acquiring a plurality K of portal images for a plurality of doses, $D^k$, k=1, ..., K, and in reference irradiation conditions;

a step (820) of removing the noise by subtracting from said portal images an image acquired in the absence of irradiation in order to obtain a plurality K of noise-suppressed images;

a step (830) of correcting noise-suppressed images in order to remove from them a component due to the backscattering by the environment of the imaging device;

a step (840) of calculating coefficients α, β from values $$\frac{D^k}{D_{10}^{eq}}$$

and $$\ln\left(\frac{N_g^k}{N_{g,10}}\right),$$

k=1, ..., K, where $N_g^k$ is the grey level of the pixel is at the centre of the kth portal image acquired.

5. Method for estimating the dose according to claim 4, characterised in that the coefficients α, β are obtained from values $$\frac{D^k}{D_{10}^{eq}}$$

and $$\ln\left(\frac{N_g^k}{N_{g,10}}\right),$$

k=1, ..., K using linear regression.

6. Method for estimating the dose according to claim 5, characterised in that said prior phase of calibration can further include a phase of validation of coefficients α, β comprising:

a step (850) of measuring the two-dimensional distribution of a dose administered at the depth of reference for each one of the doses at which the portal images were acquired, said step of measuring supplying a plurality K of measured dose images;

a step (860) of transforming acquired portal images into dose images, in order to supply a plurality K of calculated dose images;

a step (870) of comparing said measured dose images with said calculated dose images, with the coefficients α, β being validated in the event of a concordance between the first and the second.

7. Method for estimating the dose according to claim 6, characterised in that each portal image k=1, ..., K is transformed into a dose image using the relationship $$\frac{\hat{D}^k(i,j)}{D_{10}^{eq}} = \alpha + \beta\ln\left(\frac{N_g^k(i,j)}{N_{g,10}}\right)$$

where $\hat{D}^k(i,j)$ is a dose estimated for the pixel (i, j) of the kth portal image acquired and $N_g^k(i,j)$ is the grey level of the pixel (i, j) of the kth portal image acquired.

8. Method for estimating the dose according to claim 6, characterised in that the measured dose images and the calculated dose images are compared using an analysis of a gamma index (γ).

9. Method for verifying a treatment plan for an external radiotherapy system provided with a portal imaging device, with the treatment plan being defined (700) by a plurality M of two-dimensional distributions of a dose at a depth of reference, with each two-dimensional distribution being associated with an angle of incidence, a quantity of monitor units and a conformation of the irradiation beam, with each two-dimensional distribution of a dose giving a nominal dose image, said method including a calibration phase comprising:

a step (810) of acquiring a plurality K of portal images for a plurality of doses, $D^k$, k=1, ..., K, and in reference irradiation conditions;

a step (820) of removing noise by subtracting from said portal images an image acquired in the absence of irradiation in order to obtain a plurality K of noise-suppressed images;

a step (830) of correcting noise-suppressed images in order to remove from them a component due to the backscattering by the environment of the imaging device; and a step (840) of calculating coefficients α, β from values $$\frac{D^k}{D_{10}^{eq}}$$

and $$\ln\left(\frac{N_g^k}{N_{g,10}}\right),$$

k=1, ..., K, where $N_{g,10}$ is the grey level of the pixel at the centre of an image, obtained for a dose and reference irradiation conditions, $N_g^k$ is the grey level of the pixel at the centre of the kth portal image acquired, and $D_{10}^{eq}$ is a predetermined constant dose, and a verification phase comprising:

a portal image is acquired for each angle of incidence, quantity of monitor units and conformation of the irradiation beam, in such a way as to obtain the same plurality M of acquired portal images;

a transforming step in which the acquired portal images are transformed into dose images in order to supply a plurality M of calculated dose images, wherein:

said calculated dose images are compared to the nominal dose images.

10. Method for verifying a treatment plan according to claim 9, characterised in that, in the verification phase, prior to the transforming step, the background noise is removed (720) from the acquired portal images by subtracting from them an image acquired in the absence of irradiation.

11. Method for verifying a treatment plan according to claim 10, characterised in that, in the verification phase, prior to the transforming step, the acquired portal images noise-suppressed as such are corrected (730), by removing from them a component due to the backscattering of the beam by the environment of the portal imaging device.

12. Method for verifying a treatment plan according to claim 9, characterised in that the comparison between the calculated dose images and the nominal dose images is carried out using an analysis of a gamma index ($\gamma$).

13. Method for verifying a treatment plan according to claim 9, characterised in that, in the calibration phase, the coefficients $\alpha$, $\beta$ are calculated from values $$\frac{D^k}{D^{eq}_{10}}$$

and $$\ln\left(\frac{N^k_g}{N_{g,10}}\right),$$

$k=1, \ldots, K$ using linear regression.

* * * * *